United States Patent [19]

Gibson et al.

[11] 4,072,571
[45] Feb. 7, 1978

[54] KLEBSIELLA PNEUMONIAE AND ENTEROBACTER BROTH

[75] Inventors: Sandra F. Gibson, Chesterfield; Gregory D. Rodgers, Florissant, both of Mo.

[73] Assignee: McDonnell Douglas Corporation, St. Louis, Mo.

[21] Appl. No.: 682,659

[22] Filed: May 3, 1976

[51] Int. Cl.² ............................................... C12K 1/06
[52] U.S. Cl. ................................................... 195/100
[58] Field of Search ............... 195/99, 1, 103, 103.5 R

[56] References Cited
PUBLICATIONS

Robert Bailey and Elvyn Scott; Diagnostic Microbiology; Second Ed.; The C.V. Mosby Company; 1966; pp. 26, 295 and 296.

Primary Examiner—Lionel M. Shapiro
Assistant Examiner—Robert J. Warden
Attorney, Agent, or Firm—Gravely, Lieder & Woodruff

[57] ABSTRACT

A broth medium for the detection of Klebsiella, specifically *Klebsiella pneumoniae* and Enterobacter in urine. The medium employs 3-(α-acetonylbenzyl)-4-hydroxycoumarin and 2,4 dinitro-phenyl hydrazone of α-Ketoglutoric acid to inhibit growth of *Escherichia Coli* organisms and to promote growth of Klebsiella. This medium also has a pH of about 8.0 to inhibit other organisms which grow under more neutral conditions.

8 Claims, No Drawings

KLEBSIELLA PNEUMONIAE AND ENTEROBACTER BROTH

BACKGROUND OF THE INVENTION

*Klebsiella pneumoniae* and *Enterobacter* are microorganisms which occur in urine, feces, throat, etc. The presence of K. pneumoniae in urine is a reliable indicator of pneumonia. If Klebsiella or Enterobacter is present in a given sample of urine, it is also possible that *Escherichia Coli* and other coliform organisms are also present in the sample.

We desire to determine the presence of either Klebsiella or Enterobacter because these organisms, while distinct, are closely related and difficult to distinguish without extensive testing and indicate the presence of similar infections.

The medium of this invention is an improved medium designed for use with the optical detection system disclosed in U.S. applications Ser. Nos. 255,533 filed May 22, 1972 now abandoned and 461,249 filed Apr. 16, 1974 now U.S. Pat. No. 3,963,355 and in the improved devices disclosed and claimed in applications filed on even date herewith by Charles, Jones, Staples and Wiegner entitled AUTOMATED MICROBIAL ANALYZER and MACHINE AND PROCESS FOR READING CARDS CONTAINING MEDICAL SPECIMENS. These applications describe mechanism and apparatus suitable for analyzing specimens for specific microorganisms using a plastic tray or card which contains a series of dried culture media contained in separate but connected cells, each of the media being specific to a single organism. When the sample is inserted into the card, mixed with the media in the cells, and incubated in the machine, the organism (or organisms) present in the specimen interacts with the culture medium specific to that organism and produces a change in the medium which is read by the machine to indicate the presence of the organism. The change in the medium involves a change in the light transmitting properties of the medium, i.e., a color change or change in turbidity. The change may be caused by metabolic activity of the organism, which, for example, may cause production of acid and a change in pH which causes a color change in a pH sensitive indicator in the medium. The change in the light transmitting properties of the medium also could be caused by a precipitate forming in the medium due to metabolic activity of the organism or it could be caused by growth of the organism.

The specific media designed for use in the aforesaid cards are all designed to favor growth of one microorganism and to inhibit growth of other organisms, are capable of being freeze dried, and can function in the low $O_2$ environment of the wells of the card described in detail in said copending applications AUTOMATED MICROBIAL ANALYZER and MACHINE AND PROCESS FOR READING CARDS CONTAINING MEDICAL SPECIMENS.

We have discovered a medium which can selectively identify Klebsiella and Enterobacter organism in urine when the medium is placed in the wells of the cards described in application AUTOMATED MICROBIAL ANALYZER.

Positive results are indicated by means of precipitation of bile salts (sodium desoxycholate) and ricinoleic acid, which causes a change in the light transmitting character of the medium, which change is read by the mechanism described in application AUTOMATED MICROBIAL ANALYZER. The entire test can be completed within 12 – 18 hours, whereas current methods of detection require from about 36 to about 48 hours.

SUMMARY

This invention involves a broth medium for the detection of Klebsiella and Enterobacter in urine. The medium will detect the presence of *Klebsiella pneumoniae* in particular.

The medium contains sources of carbon, sources of nitrogen, sources of vitamins, bile salts mixture, E. coli inhibitors, gram-negative organism inhibitors and Klebsiella growth promoter.

The novelty of the invention lies in the use of 3-(α-acetonylbenzyl)-4-hydroxycoumarin and 2,4 dinitrophenyl hydrazone of α-Ketoglutaric acid, which operate to inhibit growth of E. Coli and promote growth of Klebsiella. The relatively high pH of the medium also helps to suppress growth of other unwanted organisms.

Also novel is the combination of Bile Salts Mixture and the ricinoleic acid indicator which allows use of the medium in the mechanism shown in application for AUTOMATED MICROBIAL ANALYZER, by means of which the presence of Klebsiella or Enterobacter is detected by precipitation in the medium.

DETAILED DESCRIPTION

The detection broth of the present invention contains from about 2.3 to about 2.8% nutrients, about 0.196 to about 0.204% 3-(α-acetonylbenzyl)-4-hydroxycoumarin and about 0.049 to about 0.051% of 2,4 dinitrophenyl hydrazone of α-Ketoglutaric acid which operate as a biological inhibitor to inhibit the growth of *E. Coli* which normally gives positive results in tests for Klebsiella or Enterobacter and which also operate to stimulate growth of Klebsiella organism. 2,4 dinitrophenyl hydrazone of α-Ketoglutaric acid also indicates the positive growth of Klebsiella organism.

The nutrient portion of the medium contains from about 4.5 to about 5.5 gm/l Gelysate, from about 9.0 to about 11.0 gm/l cellobiose, from about 9.0 to about 11.0 gm/l inositol, from about 0.24 to about 0.26 gm/l yeast extract, and from about 0.24 to about 0.26 gm/l D-biotin.

Gelysate is from BBL and is a gelatin hydrolysate made by pancreatic digestion and is low in cystine and tryptophane.

A suitable substitute for Gelysate is any nitrogen source that is free of sugar. Inorganic nitrogen sources, such as ammonium chloride, may also be used. Peptones containing low amounts of sugar may be used.

The purpose of the Gelysate is to provide nitrogen to the organism. The purpose of the cellobiose and inositol is to provide sugar to the organism, which sugar fermentation induces the dramatic change in pH which triggers the indicator.

The indicator of this invention is sodium desoxycholate and ricinoleic acid. The indicator operates by forming milky white precipitate under acid conditions. This change is observed and recorded by the mechanism described in application AUTOMATED MICROBIAL ANALYZER. The indicator mixture also acts to inhibit gram-negative organisms. From about 9.0 to about 11.0 gm/l of sodium salt of ricinoleic acid is used. Sodium hydroxide is used to adjust the pH of the medium to about 8.0.

The essence of this invention lies in the action of the chemical inhibitors, 3-(α-acetonylbenzyl)-4-hydroxycoumarin and 2,4 dinitro phenyl hydrazone of α-Ketoglutaric acid. These inhibitors act to inhibit the growth of organisms other than Klebsiella.

Growth of species of E. Coli, gram-positive organisms, and organisms which result in high yields of positives by conventional detection methods is inhibited by these chemical inhibitors in the process which uses the AUTOMATED MICROBIAL ANALYZER.

The concentration of 3-(α-acetonylbenzyl)-4-hydroxycoumarin can be from about 0.196 to about 0.204%, and it is most effective at 0.2%.

The concentration of 2,4 dinitro-phenyl hydrazone of α-Ketoglutaric acid can be from about 0.049 to about 0.051%, and it is most effective at 0.050%.

If the concentration of any inhibitor is too low, a higher yield of unwanted false positives occurs. If the concentration is too high, a lower yield occurs.

EXAMPLE 1

To prepare a 2× medium in an amount of 100 ml, Klebsiella and Enterobacter detection broth is prepared by dissolving 0.4 gm 3-(α-acetonylbenzyl)-4-hydroxycoumarin in 98 ml of distilled water by stirring with 2 ml of 1N sodium hydroxide. When the 3-(α-acetonylbenzyl)-4-hydroxycoumarin is dissolved, the following are added to the solution:

Gelysate — 1.0 gm
Cellobiose — 2.0 gm
Inositol — 2.0 gm
Yeast Extract — 0.05 gm
Sodium desoxycholate — 2.0 gm
D-Biotin — 0.05 gm
Sodium Salt of Ricinoleic Acid — 2.0 gm
2,4-dinitrophenyl hydrazone of α-Ketoglutaric acid — 5 mg The solution is then stirred for 1 hour. 2.7 mg of Brilliant Green is added to the stirred solution.

The pH of the medium is adjusted to 8.0 by means of dropwise addition of sodium hydroxide. The solution is filter sterilized.

The medium is at double (2x) the usual concentration for use in the wells and card described in application entitled AUTOMATED MICROBIAL ANALYZER.

What is claimed is:

1. A broth medium for the detection of Klebsiella or Enterobacter comprising:
   a. a nitrogen source,
   b. a carbon source,
   c. a vitamin source,
   d. a mixture of chemical inhibitors which will inhibit the growth of Escherichia Coli while simultaneously promoting the growth of Klebsiella or Enterobacter, said E. coli inhibitors being 3-(α-acetonylbenzyl) -4-hydroxycoumarin and 2,4 dinitrophenyl hydrazone of α-Ketoglutaric acid and
   e. an indicator to indicate the presence of Klebsiella or Enterobacter, at a pH of about 8.

2. The medium of claim 1 wherein about 0.196 to about 0.204% 3-(α-acetonylbenzyl)-4-hydroxycoumarin and about 0.049 to about 0.051% 2,4 dinitrophenyl hydrazone of α-Ketoglutaric acid is used.

3. The medium of claim 1 wherein the nitrogen source is Gelysate.

4. The medium of claim 1 wherein the carbon source is a mixture of cellobiose and inositol.

5. The medium of claim 1 wherein the vitamin source is a mixture of yeast extract and D-biotin.

6. A broth medium for the detection of Klebsiella or Enterobacter comprising a nitrogen source, a carbon source, a vitamin source, Escherichia Coli inhibitors, and an indicator to indicate the present of Klebsiella or Enterobacter, at a pH of 8.0, comprising a mixture of sodium desoxycholate and the sodium salt of ricinoleic acid.

7. A broth medium for the detection of Klebsiella or Enterobacter comprising per liter of medium:
   a. about 4.5 to about 5.5 gm Gelysate,
   b. about 9.0 to about 11.0 gm Cellobiose,
   c. about 9.0 to about 11.0 gm Inositol,
   d. about 0.24 to about 0.26 gm Yeast Extract,
   e. about 9.0 to about 11.0 gm sodium desoxycholate,
   f. about 0.24 to about 0.26 gm D-Biotin,
   g. about 9.0 to about 11.0 gm Sodium Salt of Ricinoleic Acid,
   h. about 1.96 to about 2.04 gm 3-(α-Acentonylbenzyl)-4- Hydroxycoumarin,
   i. about 0.49 to about 0.51 gm 2,4 dinitro-phenyl hydrazone of α-Ketoglutaric acid, and
   j. about 13.0 to about 13.5 mg/l Brilliant Green,
   k. said medium having a pH of about 8.

8. The medium of claim 7 comprising per liter of medium:
   a. 5.0 gm Gelysate,
   b. 10.0 gm Cellobiose,
   c. 10.0 gm Inositol,
   d. 0.25 gm Yeast Extract,
   e. 10.0 gm Sodium Desoxycholate,
   f. 0.25 gm D-Biotin,
   g. 10.0 gm Sodium Salt of Ricinoleic Acid,
   h. 2.0 gm 3-(α-Acetonylbenzyl)-4-Hydroxycoumarin,
   i. 0.5 gm 2,4 dinitro-phenyl Hydrazone of α-Ketoglutaric Acid, and
   j. 13.3 mg/l Brilliant Green,
   k. said medium having a pH of 8.0.

* * * * *